United States Patent
Rhodes et al.

(10) Patent No.: US 7,429,606 B2
(45) Date of Patent: Sep. 30, 2008

(54) OXADIAZOLYL-PHENOXY ALKYLISOXAZOLES, COMPOSITIONS THEREOF AND METHODS FOR THEIR USE AS ANTI-PICORNAVIRAL AGENTS

(75) Inventors: Gerald Rhodes, Los Altos, CA (US); Theodore J Nitz, Pottstown, PA (US)

(73) Assignee: ViroPharma Incorporated, Exton, PA (US)

( * ) Notice: Subject to any disclaimer, the term of this patent is extended or adjusted under 35 U.S.C. 154(b) by 686 days.

(21) Appl. No.: 10/487,852

(22) PCT Filed: Aug. 29, 2002

(86) PCT No.: PCT/US02/27537

§ 371 (c)(1),
(2), (4) Date: Sep. 28, 2004

(87) PCT Pub. No.: WO03/020271

PCT Pub. Date: Mar. 13, 2003

(65) Prior Publication Data

US 2005/0043542 A1    Feb. 24, 2005

Related U.S. Application Data

(60) Provisional application No. 60/315,615, filed on Aug. 29, 2001.

(51) Int. Cl.
*A61K 31/4245* (2006.01)
*C07D 413/02* (2006.01)
(52) U.S. Cl. ........................ 514/364; 548/143
(58) Field of Classification Search ................ 548/143; 514/364

See application file for complete search history.

(56) References Cited

U.S. PATENT DOCUMENTS 5,349,068 A * 9/1994 Diana et al. ............... 548/131
5,464,848 A   11/1995 Diana et al.

* cited by examiner

*Primary Examiner*—Kamal A Saeed
(74) *Attorney, Agent, or Firm*—Patrick J. Hagan; Dann, Dorfman, Herrell and Skillman, P.C.

(57) ABSTRACT

Oxadiazolyl-phenoxyalkylisoxazoles and pharmaceutically acceptable salts thereof, compositions comprising oxadiazolyl-phenoxyalkylisoxazole compounds or pharmaceutically acceptable salts thereof and methods for using oxadiazolyl-phenoxyalkylisoxazole compounds or pharmaceutically acceptable salts thereof as anti-picornaviral agents are described herein. The methods include using pleconaril as a prodrug for conversion to anti-picornaviral compounds in vivo.

17 Claims, No Drawings

OXADIAZOLYL-PHENOXY ALKYLISOXAZOLES, COMPOSITIONS THEREOF AND METHODS FOR THEIR USE AS ANTI-PICORNAVIRAL AGENTS

This application is a national stage filing under 35 U.S.C. § 371 of PCT International Application PCT/US02/27537, filed Aug. 29, 2002 which in turn claims benefit under 35 U.S.C § 119 (e) of U.S Provisional Application No 60/315,615, filed Aug. 29, 2001, the entire contents of which are incorporated herein by reference.

1. FIELD OF THE INVENTION

The present invention relates to oxadiazolyl-phenoxyalkylisoxazoles and pharmaceutically acceptable salts thereof, compositions comprising oxadiazolyl-phenoxyalkylisoxazole compounds or pharmaceutically acceptable salts thereof, and methods for using oxadiazolyl-phenoxyalkylisoxazole compounds or pharmaceutically acceptable salts thereof as anti-picornaviral agents.

2. BACKGROUND OF THE INVENTION

Picornaviridae are a large group of single-stranded RNA viruses that cause infections such as viral meningitis, encephalitis, viral respiratory infection and viral exacerbation in asthma and colds (*Picornaviridae and Their Replication*; Second Edition, edited by B. N. Fields et al., New York, 1990). Picornaviruses were among the first viruses recognized and encompass approximately 230 serotypes divided into five genera that include apthovirus, cardiovirus, enterovirus, hepatovirus and rhinovirus. Enterovirus and rhinovirus, which cause the common cold, comprise most of the known picornavirus serotypes.

The replication of single-stranded RNA viruses such as picornaviruses occurs entirely in the cytoplasm and has been well characterized. Briefly, the genome of picornaviruses consists of one single-stranded (+)-sense RNA molecule that encodes a single polyprotein, typically between about 2100 amino acids and about 2400 amino acids in length. The polyprotein is processed through proteolytic cleavage to provide viral proteins such as a picornavirus protease, a virus RNA-dependent RNA polymerase and various coat proteins. The cleavage of the polyprotein into the above proteins is highly specific and may provide an attractive target for pharmaceutical intervention. A significant problem in developing effective pharmaceutical treatment of picornaviral infections, however, is the rapid mutation rate of RNA viruses. This rapid mutation rate might be caused by the absence of any error-correcting mechanisms in RNA synthesis.

The cellular receptors of a number of different picornaviruses have been identified using a number of conventional techniques (for example, binding competition between different viruses, monoclonal antibodies that prevent virus binding and fluorescently labeled virus). Prevention of virus binding to cellular receptors is another attractive area for pharmaceutical intervention (Heinz et al., *J. Virol.*, 1989, vol. 63, pp. 2476). Picornaviruses have also been characterized by X-ray crystallography (Rossman et al., *Nature*, 1985, 317, 145), which has been of great value in rationally designing inhibitors that interfere with virus-receptor binding.

Picornaviruses, particularly those of enterovirus and rhinovirus genera cause significant numbers of human viral infections each year. Effective therapies for the majority of picornaviral infections are inadequate or simply unavailable.

Thus, there is a general need for agents active against picornaviruses and a specific need for agents active against enteroviruses and rhinoviruses.

U.S. Pat. No. 4,843,087 discloses diheterocylic compounds for use as anti-viral agents. U.S. Pat. Nos. 5,349,068 and 5,464,848 disclose 1,2,4-oxadiazolyl-phenoxyalkylisoxazoles and their use as anti-picornaviral agents.

Citation or identification of any reference in Section 2. of this Application is not an admission that any such reference is available as prior art to the present invention.

3. SUMMARY OF THE INVENTION

The present invention provides the compounds of Formula I and Formula II:

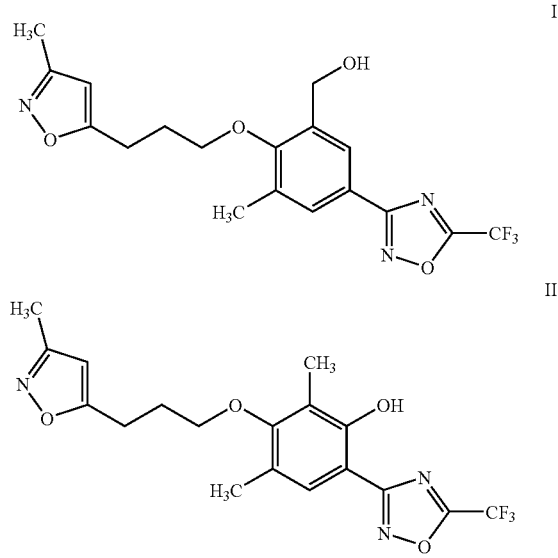

and pharmaceutically acceptable salts thereof.

The compounds of Formula I and Formula II and pharmaceutically acceptable salts thereof are useful as anti-picornaviral agents.

In a second aspect, the present invention provides compositions comprising a therapeutically effective amount of a compound of Formula I or Formula II, or a pharmaceutically acceptable salt thereof. The compositions optionally comprise a pharmaceutically acceptable vehicle. The compositions are useful for treating or preventing a picornaviral infection in a patient.

In a third aspect, the present invention provides methods for treating or preventing a picornaviral infection in a patient, comprising administering to a patient in need of such treatment or prevention an effective amount of a compound of Formula I or Formula II or a pharmaceutically acceptable salt thereof.

In a fourth aspect, the present invention provides methods for treating or preventing a picornaviral infection in a patient, comprising administering to a patient in need of such treatment or prevention an effective amount of pleconaril as a prodrug for compounds of Formula I or Formula II. The pleconaril prodrug preferably is administered as a pharmaceutically acceptable composition of pleconaril and/or pharmaceutically acceptable salts thereof.

In a fifth aspect, the present invention provides methods for inhibiting the growth of a picornavirus in a cell comprising contacting a cell infected with a picornavirus with an effective amount of a compound of Formula I or Formula II or a pharmaceutically acceptable salt thereof.

Other aspects and features of the inventions are described herein below.

4. DETAILED DESCRIPTION OF THE INVENTION

The present invention provides the novel compounds of Formula I and Formula II:

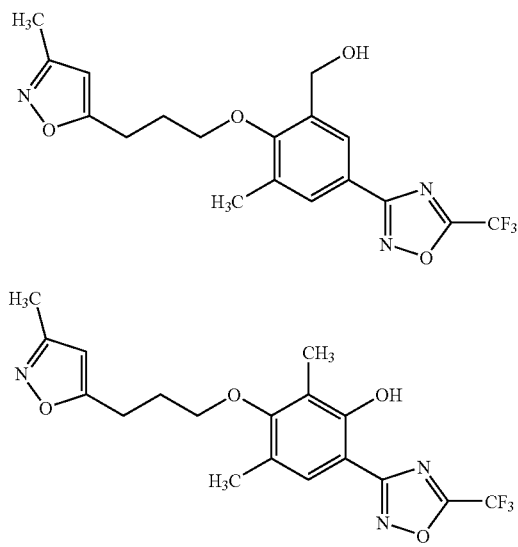

and pharmaceutically acceptable salts thereof.

The compounds of Formulas I and II and pharmaceutically acceptable salts thereof are useful as anti-picornaviral agents, preferably human anti-viral agents. The compounds may be prepared synthetically and formulated prior to administration or other use. Otherwise the compounds may be generated in vivo by the metabolism of pleconaril and used immediately, or obtained as in a metabolic state, collected, purified and isolated, if necessary, as a metabolite.

4.1 Definitions and Abbreviations

As used herein, the term "compounds of the invention" means, collectively, the compounds of Formulas I and II, pharmaceutically acceptable salts thereof, and mixtures thereof. The compounds of the invention are identified herein by their chemical structure and/or chemical name. Where a compound is referred to by both a chemical structure and a chemical name, and that chemical structure and chemical name conflict, the chemical structure is determinative of the compound's identity. The chemical structures depicted herein and the compounds of the invention also encompass all of the corresponding compounds' possible tautomeric forms. Such tautomers may, in certain instances, be resolved into individual compounds by methods known to those of skill in the art.

When administered to a patient, for example, to an animal for veterinary use or for improvement of livestock, or to a human for clinical use, the compounds of the invention are preferentially administered in isolated form. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single oxadiazolyl-phenoxyalkylisoxazole compound of the invention by weight of the isolate.

The phrase "pharmaceutically acceptable salt(s)," as used herein includes but is not limited to salts of acidic or basic groups that may be present in compounds used in the present compositions. Compounds included in the present compositions include salts formed with the basic moieties in the compounds, for example salts formed with various inorganic and organic acids found in vivo or otherwise. The acids that may be used to prepare pharmaceutically acceptable acid addition salts of such basic compounds are those that form non-toxic acid addition salts, that is, salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (that is, 1,1'-methylene-bis-(2-hydroxy-3-naphthoate)) salts. The present compositions of the compounds include the situation wherein the acidic moieties of the compounds form base salts with various pharmacologically acceptable cations or other cations found in vivo or otherwise. Examples of such salts include alkali metal or alkaline earth metal salts and, particularly, calcium, magnesium, sodium, lithium, zinc, potassium, and iron salts.

Examples of picornaviruses include but are not limited to enteroviruses, echoviruses, coxsackie virus and rhinovirus. Human rhinovirus serotypes ("HRV") include, but are not limited to, HRV-2, -14, -1A, -1B, -6, -21, -22, -15, -25, -30, -50, -67, -89, -86 and -41 and HRV-3, -4, -5, -9, -16, -18, -38, -66, -75 and -61.

4.2 Synthesis of the Compounds of the Invention

The compounds of the invention can be obtained via the synthetic methodology illustrated in Schemes A through E. Starting materials useful for preparing the compounds of the invention and intermediates therefore, are commercially available or can be prepared by well known synthetic methods.

Scheme A

The compound of Formula I can be prepared via the following process:

(a) Preparation of the Bromophenol:

The bromophenol is prepared by protecting the hydroxyalkyl group with a substituted silyl, wherein R is a lower alkyl ($C_1$-$C_6$) or phenyl, for example dimethyl, t-butyl silyl or diphenyl silyl; in the presence of diisopropylethylamine (DIPEA) or imidazole:

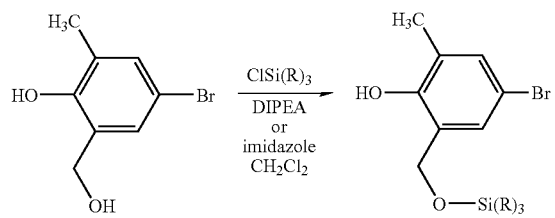

(b) Preparation of the Cyanophenol:

The bromophenol reacts with the a cyanide salt, for example, zinc cyanide, potassium cyanide or cuprous cyanide; in an inert solvent for example, in dimethylformamide (DMF), N-methylpyrrolidinone (NMP), or p-dioxane; at an elevated temperature, with a palladium catalyst, such as tetrakis(triphenylphosphine)palladium(0); to give the cyanophenol:

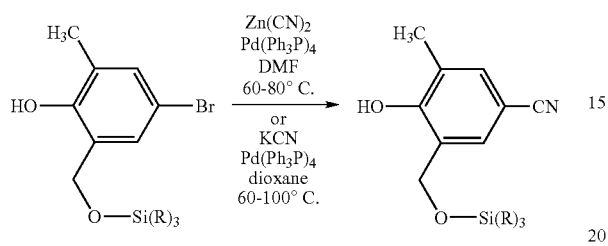

(c) Preparation of the Cyano Compound:

The cyanophenol reacts with the haloisoxazole, where X is chloro, bromo or iodo; in a dry polar inert solvent, for example N,N-dimethylformamide or N-methylpyrrolidinone; in the presence of base, such as potassium carbonate; optionally in the presence of a catalytic amount of potassium or sodium iodide; at an elevated temperature (50° C. to 120° C.) to give the cyano compound:

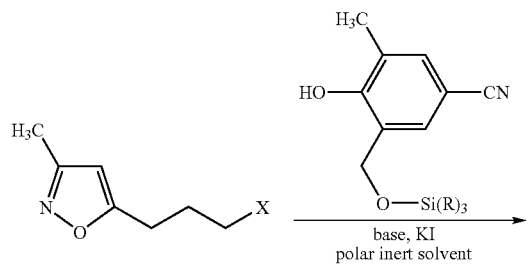

(d) Preparation of the Amidoxime:

The cyano compound reacts with hydroxylamine hydrochloride in the presence of base, for example, triethylamine (TEA), potassium or sodium carbonate, or sodium acetate; in an alcoholic solvent, for example, ethyl, propyl, isopropyl, or butyl alcohol; at room temperature to ref lux to give the amidoxime:

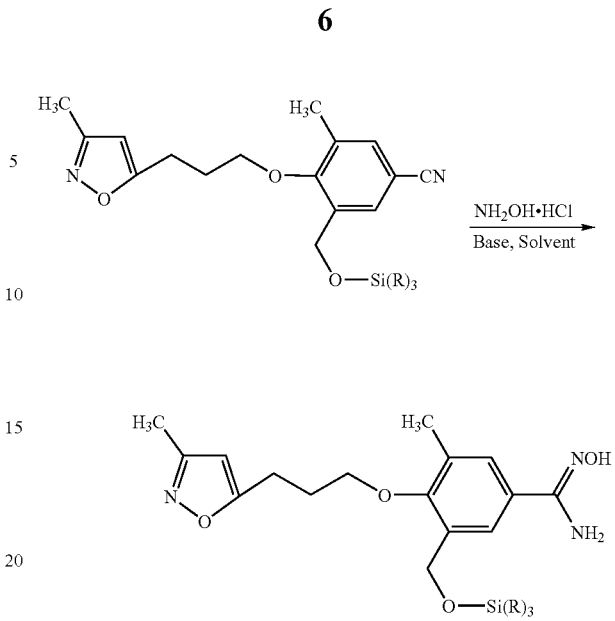

(e) Preparation of (O-silyl)(oxadiazolyl)-phenoxyalkyl-isoxazole:

The next step involves one of the following methods. In one method, the amidoxime is reacted with the acid halide or the acid anhydride in the presence of an organic or inorganic base, such as pyridine, triethylamine, or potassium carbonate; in an inert solvent, for example, N,N-dimethylformamide, acetone, isopropylacetate, N-methylpyrrolidinone, methylene chloride, chloroform, toluene, or tetrahydrofuran (THF), or in a base which also functions as the solvent, such as pyridine; at room temperature to reflux temperature or at a reduced temperature (about 0° C. to 15° C.), so as to yield the desired (O-silyl) (oxadiazolyl)-phenoxyalkylisoxazole. In the latter case, an intermediate O-acyl derivative is isolated and heated at a temperature in the range of about 100° C. to 130° C., for a time sufficient for cyclization to the oxadiazole of Formula I to occur, generally about 5 minutes to 4 hours.

In another method, the amidoxime is reacted with the acid halide or acid anhydride in an acid which corresponds to the acid halide or acid anhydride at an elevated temperature (about 70° C. to 100° C.):

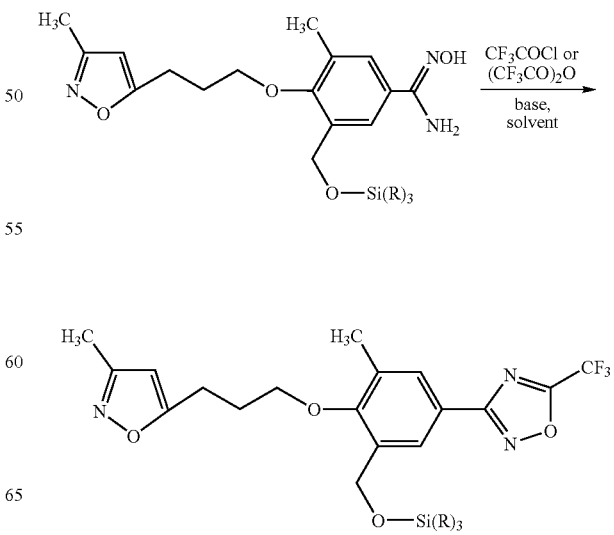

In another method, the amidoxime is reacted neat with an ester, $CF_3CO_2R_6$, wherein $R_6$ is a lower alkyl or phenyl, or additionally with N,N-dimethylformamide or N-methylpyrrolidinone to solubilize the reaction mixture; at elevated temperatures (about 105° C.):

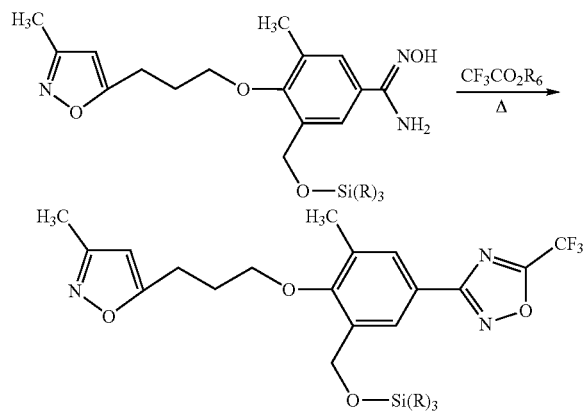

(f) Preparation of the Compound of Formula I:

In the last step, the protecting group is removed from the (O-silyl)(oxadiazolyl)-phenoxyalkylisoxazole with potassium fluoride or cesium fluoride in N,N-dimethylformamide, or with hydrofluoric acid or hydrochloric acid in water and acetonitrile or tetrahydrofuran:

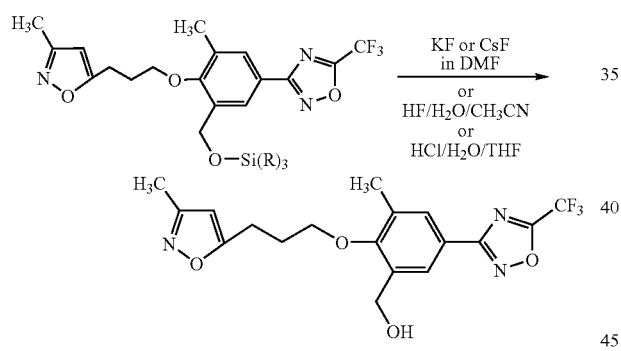

Scheme B

The compound of Formula I can also be prepared by the following method:

(a) Preparation of the hydroxyalkyl-cyanophenol:

The hydroxyalkyl-phenol is prepared by treating the cyanophenol with formaldehyde under Lewis Acid conditions, for example with aluminum chloride, tin chloride, or ferric chloride; in an inert solvent:

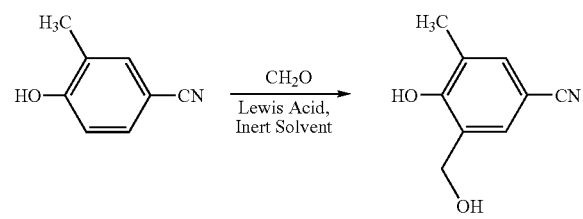

(b) Preparation of the Protected hydroxyalkyl-cyanophenol:

The protected hydroxyalkyl-cyanophenol is prepared by protecting the hydroxyalkyl group with a substituted silyl, wherein R is a lower alkyl ($C_1$-$C_6$) or phenyl, such as dimethyl, t-butyl silyl or diphenyl silyl; in the presence of diisopropylethylamine (DIPEA) or imidazole; in an inert solvent:

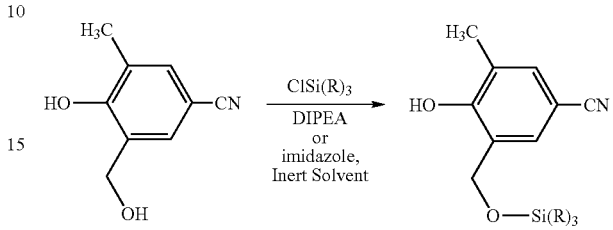

(c) Preparation of cyano-alkyne:

The resulting protected hydroxyalkyl-cyanophenol, from step (b) above, reacts with the haloalkyne, where X is chlorine or bromine; in the presence of base, such as potassium carbonate; optionally with a catalytic amount of potassium iodide; in an inert polar solvent, for example N-methylpyrrolidinone, N,N-dimethylformamide, or methylene chloride; at a temperature in the range from about room temperature to 120° C. to form the cyano compound:

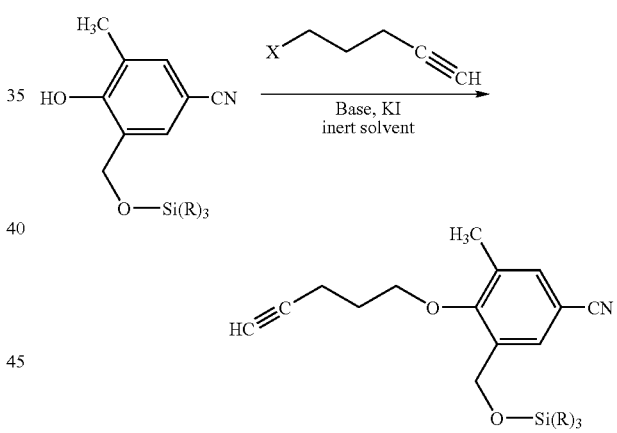

The cyano compound reacts with hydroxylamine hydrochloride in the presence of base, such as triethylamine, sodium acetate, sodium carbonate; in an alcoholic solvent, for example, ethyl alcohol; at a temperature in the range from about room temperature to about 150° C. to form the amidoxime:

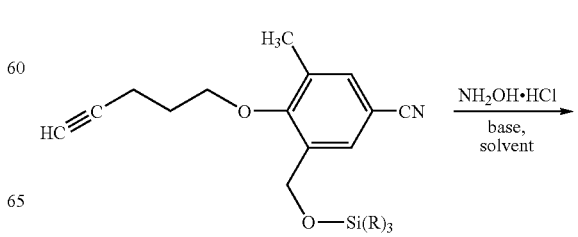

-continued

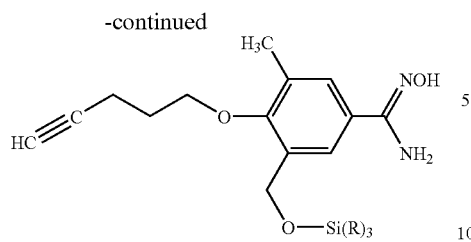

(d) Preparation of Imidazole Intermediate:

The amidoxime reacts with the acid anhydride in a basic solvent, such as pyridine; at an elevated temperature (about 80° C. to 130° C.) and in an inert solvent such as isopropyl acetate; to form the imidazole intermediate:

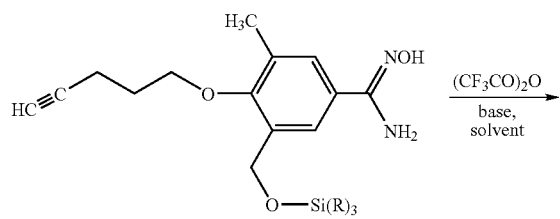

(e) Preparation of the Compound of Formula I:

The compound of Formula I is then prepared by reacting the imidazole intermediate with a nitrile oxide which is prepared in situ from a hydroxyimino halide of the formula CH₃C(X)=NOH, where X is chlorine or bromine; which may be prepared in situ, in the presence of an amine base, such as triethylamine, diisopropylethylamine, pyridine or N-methylpyrrolidinone. The hydroxyimino halide is readily prepared by conventional procedures, for example, by reacting an aldehyde oxime (CH₃CH=NOH) with a halogenating agent, such as N-chlorosuccinimide (NCS) or bromine. This process takes place by mixing the aldehyde oxime and halogenating agent in an inert polar solvent, such as dimethylformamide, N-methylpyrrolidinone, or tetrahydrofuran; then heating the mixture with the imidazole intermediate in the presence of base, for example, triethylamine:

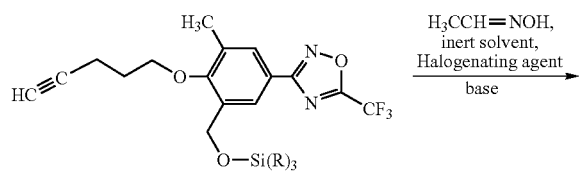

-continued

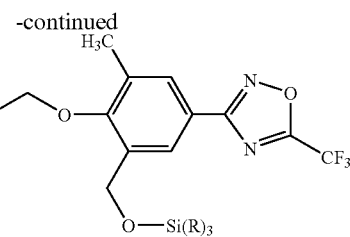

Deprotection is carried out as previously described.

Scheme C

The compound of Formula II can be prepared by the following method:

(a) Preparation of the Intermediate Isoxazole:

The intermediate isoxazole is prepared by reacting the phenol with the isoxazole in the presence of diethyl azodicarboxylate (DEAD) and triphenylphosphine [(Ph)₃P] in an inert solvent, such as tetrahydrofuran, chloroform, dimethylformamide or N-methylpyrrolidinone; at a temperature in the range of from about −20° C. to about 20° C.:

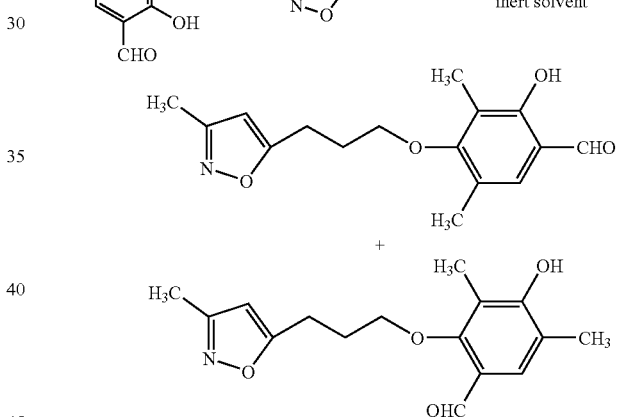

As an alternative, the intermediate isoxazole can be prepared by reacting the phenol with a haloisoxazole, where X is chloro, bromo or iodo; in a dry inert solvent, such as N,N-dimethylformamide, acetonitrile, or N-methylpyrrolidinone; in the presence of base, for example, potassium carbonate; optionally in the presence of a catalytic amount of potassium or sodium iodide; at an elevated temperature (50° C. to 120° C.) to give the cyano compound:

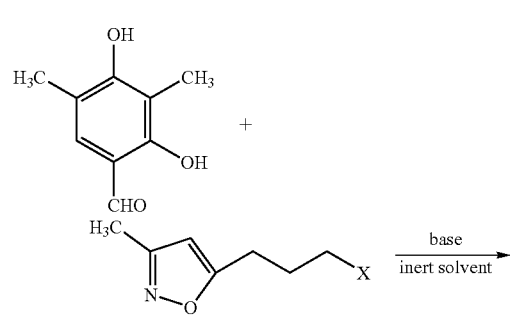

-continued

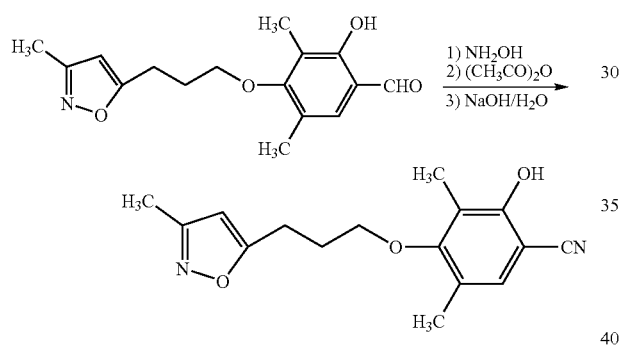

The appropriate intermediate isoxazole can be isolated and purified before the next step by using known separation techniques (b) Preparation of the Cyano Compound:

The cyano compound is prepared through conversion of the aldehyde to the oxime, followed by dehydration of the oxime with acetic anhydride. A rinse with sodium hydroxide removes the ancillary acetate:

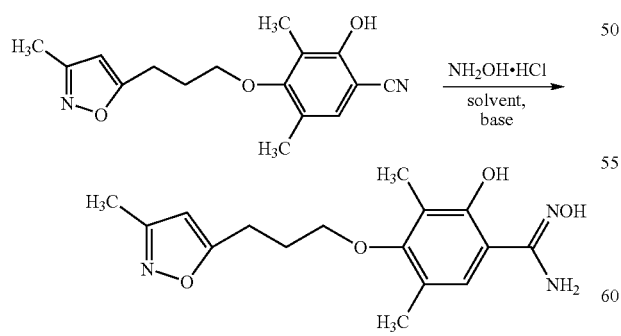

(c) Preparation of the Amidoxime:

The cyano compound reacts with hydroxylamine hydrochloride in the presence of a base, such as triethylamine, potassium or sodium carbonate, or sodium acetate; in an alcoholic solvent, such as ethyl or butyl alcohol; at an elevated temperature (50° C. to 150° C.) to give the amidoxime:

The amidoxime reacts with the acid anhydride in a basic solvent, such as pyridine; in an inert solvent, such as isopropyl acetate; at an elevated temperature (about 80° C. to 130° C.) to form the compound of Formula II:

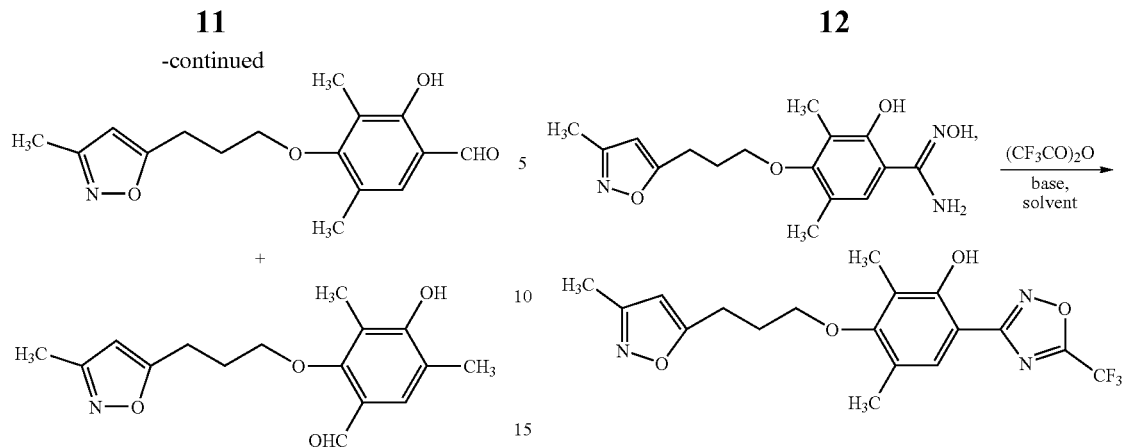

Scheme D

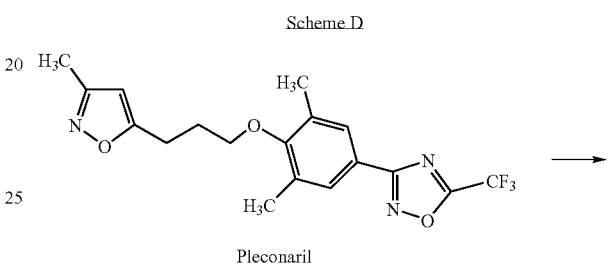

Pleconaril

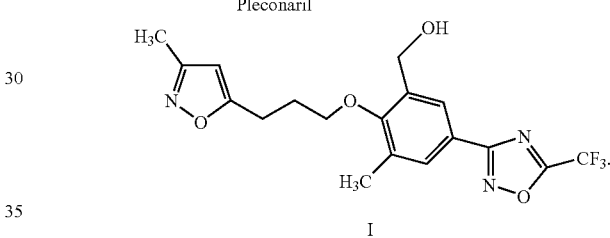

I

Scheme E

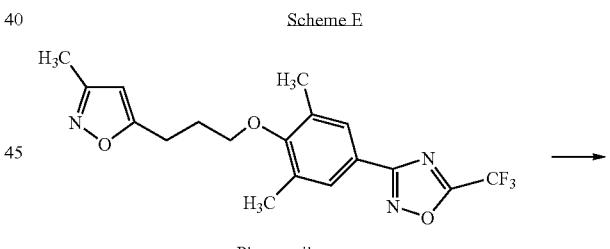

Pleconaril

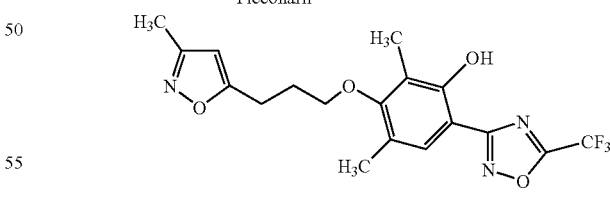

II

Schemes D and E involve the in vivo metabolism of pleconaril to form compounds of the invention.

4.3 Therapeutic Uses of the Compounds of the Invention

In practicing the present invention, a compound of the invention is administered to a patient, preferably a human, infected with a picornaviral infection. In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In another embodiment, "treatment" or "treating" refers to an amelioration of at least one physical parameter or one symptom, not necessarily discernible by the patient or by direct analytical methods but which may be inferred by extrapolation. In yet another embodiment, "treatment" or "treating" refers to inhibiting the progression of a disease or disorder, either physically, for example, stabilization of a discernible symptom, physiologically, for example, stabilization of a physical parameter, or both. In yet another embodiment, "treatment" or "treating" refers to delaying the onset of a disease or disorder.

In certain embodiments, the compounds of the invention are administered to a patient, preferably a human, as a preventative measure against such diseases. As used herein, "prevention" or "preventing" refers to a reduction of the risk of acquiring a given disease or disorder. In a preferred mode of the embodiment, the compositions of the invention are administered as a preventative measure to a patient, preferably a human, having a predisposition to a picornaviral infection.

4.4 Therapeutic/Prophylactic Administration and Compositions

Due to the activity of the-compounds of the invention, the compounds are advantageously used in veterinary and human medicine. As described above, the compounds of the invention are useful for the treatment or prevention of picornaviral infections.

The invention provides methods of treatment and prophylaxis by administration to a patient of a therapeutically effective amount a compound of the invention. The patient is an animal, including, but not limited, to an animal such a cow, horse, sheep, pig, chicken, turkey, quail, cat, dog, mouse, rat, rabbit and guinea pig and is preferably a mammal, more preferably a primate and most preferably a human.

The compounds of the invention may be administered as such, or in the form of a precursor from which the active agent can be derived, such as a prodrug. A prodrug is a derivative of a compound described herein, the pharmacologic action of which results from the conversion by chemical or metabolic processes in vivo to the active compound. Prodrugs include, without limitation, pleconaril, which can be prepared according to procedures in U.S. Pat. No. 5,464,848 which is hereby incorporated-by-reference in its entirety.

The present compositions, which comprise a compound of the invention, or a suitable prodrug, and optionally a pharmaceutically acceptable vehicle, are preferably administered orally. An especially preferred feature of the invention is the method of using pleconaril to prepare in vivo one or more of the compounds of Formula I or II. The compounds of the invention, can be administered by any other convenient route, for example, by infusion or bolus injection, by absorption through epithelial or mucocutaneous linings (for example, oral mucosa, rectal and intestinal mucosa) and may optionally be administered together with another biologically active agent. Administration can be systemic or local. Various delivery systems are known, for example, encapsulation in liposomes, microparticles, microcapsules and capsules and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectal, by inhalation, or topically, particularly to the ears, nose, eyes, or skin. Modes of administration are left to the discretion of the practitioner and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, for example, in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce compounds of the invention into the central nervous system by any suitable route, including intraventricular, intrathecal and epidural injection. Intraventricular injection can be facilitated by an intraventricular catheter, for example, attached to a reservoir, such as an Ommaya reservoir.

Pulmonary administration can also be employed, for example, by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled-release system. In one embodiment, a pump can be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity to the target of the compounds of the invention, for example, the liver, thus requiring only a fraction of the systemic dose (see, for example, Goodson, in Medical Applications of Controlled Release, supra, vol. 2, pp. 115-138 (1984)). Other controlled-release systems discussed in the review by Langer, 1990, *Science* 249:1527-1533) can be used.

The present compositions contain a therapeutically effective amount of a compound of the invention, preferably in purified form, and optionally together with a suitable amount of a pharmaceutically acceptable vehicle so as to provide the form for proper administration to the patient.

In a specific embodiment, the term "pharmaceutically acceptable" means approved by a regulatory agency of the Federal or a state government, listed in the U.S. Pharmacopeia or other generally recognized pharmacopeia for use in animals and more particularly in humans; or generally regarded by those of skill in the art as being safe to a patient. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see for example, U.S. Pat. No. 5,698,155). Other examples of suitable pharmaceutical vehicles are described in "Remington's Pharmaceutical Sciences" Gennard A. R., (Ed.), Mack Publishing Co., Pennsylvania (1985).

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the components of the present compositions are supplied either separately or mixed together in unit dosage form, for example, as a dry lyophilized powder or water free concentrate in a hermetically sealed container such as an ampoule or sachette indicating the quantity of active agent. Where a compound of the invention is to be administered by infusion, it can be dispensed, for example, with an infusion bottle containing sterile pharmaceutical-grade water or saline. Where a compound of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard vehicles such as mannitol, lactose, starch, magnesium stearate, sodium saccharin, cellulose and magnesium carbonate. Such vehicles are preferably of pharmaceutical grade.

The amount of a compound of the invention or the pleconaril prodrug that will be effective in the treatment of a picornaviral infection will depend on the nature of the infection and can be determined by standard clinical techniques. In addition, in vitro or in vivo assays can optionally be employed to help identify optimal dosage ranges. The precise dose to be employed will also depend on the route of administration and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In specific preferred embodiments of the invention, the oral dose is 0.01 milligram to 70 milligrams per kilogram body weight, more preferably 0.1 milligram to 50 milligrams per kilogram body weight, more preferably 0.5 milligram to 20 milligrams per kilogram body weight, and yet more preferably 1 milligram to 10 milligrams per kilogram body weight. In a most preferred embodiment, the oral dose is 5 milligrams of a compound of the invention per kilogram body weight.

An example of a recommended oral dosing regime is 400 mg of pleconaril (two 200 mg tablets) three times daily (TID) for 5 days. On the first day of treatment, three doses should be taken with a minimum of three hours between doses. Pleconaril tablets should be taken with a meal or a snack to improve absorption.

The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from doseresponse curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for picornaviral infection. The compounds of the invention may also be demonstrated to be effective and safe using animal model systems.

Because compounds within the scope of the invention are able to suppress the growth of viruses when added to a medium in which the virus is growing, it is specifically contemplated that compounds of the invention can therefore be used in aqueous solution, optionally, in the presence of a surfactant, to decontaminate surfaces on which viruses, including polio and picornaviruses are present, such surfaces including, but not limited to, hospital glassware, hospital working surfaces and similar areas in the preparation of food.

Hand contact of nasal mucus is an important mode of picornaviral, particularly, rhinoviral transmission. Disinfection and/or sterilization of the hands of people coming into contact with persons infected with a picornavirus would be a method useful for preventing further spread of the disease. If a compound of the invention were incorporated into a hand-washing procedure or hand-care composition, such procedure or composition may inhibit replication of picornaviruses and decrease the likelihood of the transmission of the disease.

Where a compound of the invention is administered prior to infection, that is, prophylactically, it is preferred that the administration be performed within 0 to 48 hours prior to infection of the host animal with the pathogenic virus. Where a compound of the invention is administered therapeutically to inhibit replication of a picornavirus or progression of infection, it is preferred that the administration be performed within about a day or two after infection with the pathogenic virus.

Other methods will be known to the skilled artisan and are within the scope of the invention.

4.5 Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, a compound of the invention is administered concurrently with the administration of another therapeutic agent, which can be administered as a component of a composition comprising the compound of the invention or as a component of a different composition. In another embodiment, a composition comprising a compound of the invention is administered prior or subsequent to administration of another therapeutic agent. In certain embodiments, where a compound of the invention is administered in combination with another therapeutic agent that potentially produces adverse side effects including but not limited to toxicity, the therapeutic agent can advantageously be administered at a dose that falls below the threshold at which the adverse side is elicited.

5. EXAMPLE

The following pharmaceutical formulation may be used as a prodrug pharmaceutical composition: A tablet formulation for oral administration containing 200 mg of pleconaril, and the following inactive ingredients: lactose, starch, crospovidone, sodium lauryl sulfate, colloidal silicon dioxide, and magnesium stearate.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited in the foregoing specification, the entire disclosure of which are incorporated by reference herein.

What is claimed is:

1. The compound of Formula I:

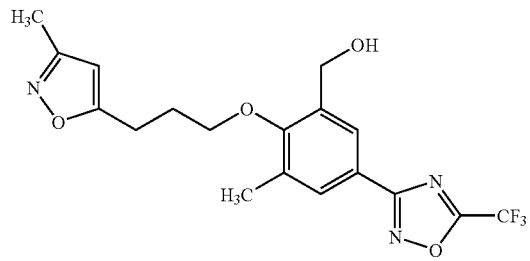

or a pharmaceutically acceptable salt thereof.

2. The compound of Formula II:

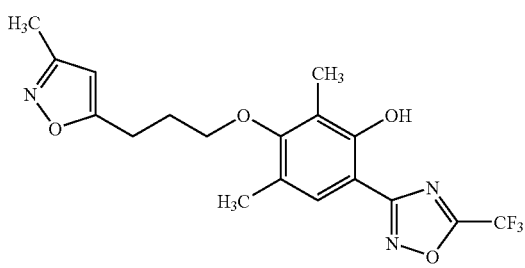

or a pharmaceutically acceptable salt thereof.

3. A composition comprising a compound according to claim 1 or a pharmaceutically acceptable salt thereof.

4. A composition comprising a compound according to claim 2 or a pharmaceutically acceptable salt thereof.

5. The composition according to claim 3, further comprising a pharmaceutically acceptable vehicle.

6. The composition according to claim 4, further comprising a pharmaceutically acceptable vehicle.

7. A method for treating a picornaviral infection in a patient, said method comprising administering to a patient in need of such treatment a therapeutically effective amount of the compound according to claim 1 or a pharmaceutically acceptable salt thereof.

8. A method for treating a picornaviral infection in a patient, said method comprising administering to a patient in need of such treatment a therapeutically effective amount of the compound according to claim 2 or a pharmaceutically acceptable salt thereof.

9. A method for inhibiting the growth of a picornaviral infection in a cell, said method comprising contacting a cell infected with a picornavirus with an inhibitory amount of the compound according to claim 1 or a pharmaceutically acceptable salt thereof.

10. A method for inhibiting the growth of a picornaviral infection in a cell, said method comprising contacting a cell infected with a picornavirus with an inhibitory amount of the compound according to claim 2 or a pharmaceutically acceptable salt thereof.

11. A method according to claim 7, wherein a precursor of said compound is administered in the form of a prodrug.

12. A method according to claim 8, wherein a precursor of said compound is administered in the form of a prodrug.

13. A method according to claim 11, wherein said prodrug is pleconaril.

14. A method according to claim 12, wherein said prodrug is pleconaril.

15. A method of using pleconaril as a prodrug for treating picornaviral infections in a patient, said method comprising administering to said patient a therapeutically effective amount of pleconaril or a pharmaceutically acceptable salt thereof.

16. A method of using pleconaril as a prodrug for treating a patient infected with at least one picornavirus, said method comprising administering to said patient a therapeutically effective amount of pleconaril or a salt thereof whereby said administrating results in the in vivo production of the compound of Formula I:

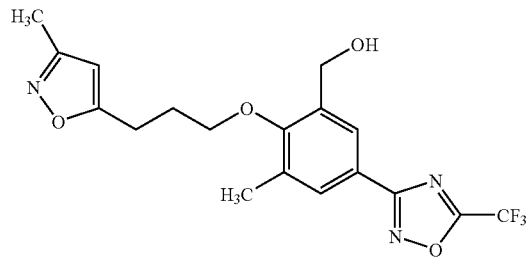

or a salt thereof.

17. A method of using pleconaril as a prodrug for treating a patient infected with at least one picornavirus, said method comprising administering to said patient a therapeutically effective amount of pleconaril or a salt thereof whereby said administrating results in the in vivo production of the compound of Formula II:

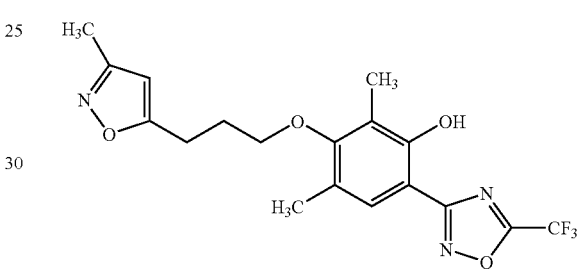

or a salt thereof.

* * * * *